(12) United States Patent
Ottma et al.

(10) Patent No.: US 8,679,174 B2
(45) Date of Patent: Mar. 25, 2014

(54) CATHETER FOR THE TRANSVASCULAR IMPLANTATION OF PROSTHETIC HEART VALVES

(75) Inventors: Rüdiger Ottma, Groβschwabhausen (DE); Robert Moszner, Bad Klosterlausnitz (DE); Hans-Reiner Figulla, Jena (DE); Markus Ferrari, Jena (DE); Christoph Damm, Jena (DE)

(73) Assignee: JenaValve Technology, GmbH, Munich (DE)

( * ) Notice: Subject to any disclaimer, the term of this patent is extended or adjusted under 35 U.S.C. 154(b) by 1357 days.

(21) Appl. No.: 11/795,590

(22) PCT Filed: Jan. 12, 2006

(86) PCT No.: PCT/DE2006/000056
§ 371 (c)(1),
(2), (4) Date: Jun. 5, 2008

(87) PCT Pub. No.: WO2006/076890
PCT Pub. Date: Jul. 27, 2006

(65) Prior Publication Data
US 2009/0234443 A1 Sep. 17, 2009

(30) Foreign Application Priority Data
Jan. 20, 2005 (DE) .......................... 10 2005 003 632

(51) Int. Cl.
*A61F 2/24* (2006.01)
(52) U.S. Cl.
USPC ...................................... 623/2.11
(58) Field of Classification Search
USPC ......... 606/108, 140–143, 153, 200; 623/1.11, 623/1.23, 2.11, 23.72
See application file for complete search history.

(56) References Cited

U.S. PATENT DOCUMENTS

| 4,922,905 A | 5/1990 | Strecker |
|---|---|---|
| 5,002,566 A | 3/1991 | Carpentier et al. |

(Continued)

FOREIGN PATENT DOCUMENTS

| AU | 2006310681 A1 | 5/2007 |
|---|---|---|
| CA | 2436258 A1 | 1/2005 |

(Continued)

OTHER PUBLICATIONS

File history for German Patent DE 195 46 692 filed Dec. 14, 1995 and patented Jul. 11, 2002.

(Continued)

*Primary Examiner* — Melanie Tyson
(74) *Attorney, Agent, or Firm* — Bookoff McAndrews, PLLC

(57) ABSTRACT

A catheter for the transvascular implantation of prosthetic heart valves, including self-expanding anchorage supports, which allow a minimally invasive implantation of prosthetic heart valves to reduce the risk to the patient during the implantation. A prosthetic heart valve including anchorage supports is temporarily housed in a folded form in a cartridge-type unit during the implantation. The cartridge-type unit can be fixed on the proximal end of a guide system, which includes a flexible region that can be guided through the aorta. Actuating elements run through the interior of the hollow guide system, permitting sections of the cartridge-type unit to be displaced radially about their longitudinal axis and/or laterally in a proximal direction, thus allowing individual sections of the anchorage support and the associated prosthetic heart valve to be sequentially released.

34 Claims, 6 Drawing Sheets

(56) References Cited

U.S. PATENT DOCUMENTS

| | | |
|---|---|---|
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,411,552 A | 5/1995 | Andersen et al. |
| 5,456,713 A | 10/1995 | Chuter |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenblit et al. |
| 5,880,242 A | 3/1999 | Hu et al. |
| 5,885,238 A | 3/1999 | Stevens et al. |
| 5,899,936 A | 5/1999 | Goldstein |
| 5,928,281 A | 7/1999 | Huynh et al. |
| 5,935,163 A | 8/1999 | Gabbay |
| 5,104,407 B1 | 9/1999 | Lam et al. |
| 6,001,126 A | 12/1999 | Nguyen-Thien-Nhon |
| 5,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,273,876 B1 | 8/2001 | Klima et al. |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 2001/0011187 A1 | 8/2001 | Pavcnik et al. |
| 2001/0039450 A1 | 11/2001 | Pavcnik et al. |
| 2002/0032481 A1 | 3/2002 | Gabbay |
| 2002/0055775 A1 | 5/2002 | Carpentier et al. |
| 2002/0120322 A1 | 8/2002 | Thompson et al. |
| 2002/0123790 A1 | 9/2002 | White et al. |
| 2002/0133226 A1 | 9/2002 | Marquez et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0044350 A1* | 3/2004 | Martin et al. .............. 606/139 |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0093063 A1* | 5/2004 | Wright et al. ............. 623/1.12 |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller |
| 2004/0210304 A1 | 10/2004 | Seguin et al. |

(56) References Cited

U.S. PATENT DOCUMENTS

| | | |
|---|---|---|
| 2004/0243143 A1 | 12/2004 | Corcoran et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075776 A1 | 4/2005 | Cho |
| 2005/0096726 A1 | 5/2005 | Sequin et al. |
| 2005/0096736 A1 | 5/2005 | Osse et al. |
| 2005/0098547 A1 | 5/2005 | Cali et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0074484 A1 | 4/2006 | Huber |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0193885 A1 | 8/2006 | Neethling et al. |
| 2006/0210597 A1 | 9/2006 | Hiles |
| 2006/0224183 A1 | 10/2006 | Freudenthal |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0088431 A1 | 4/2007 | Bourang et al. |
| 2007/0093887 A1 | 4/2007 | Case et al. |
| 2007/0100435 A1 | 5/2007 | Case et al |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stobie |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0133003 A1 | 6/2008 | Seguin et al. |
| 2008/0140189 A1 | 6/2008 | Nguyen et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0255660 A1 | 10/2008 | Guyenot et al. |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0222076 A1 | 9/2009 | Figulla et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |

FOREIGN PATENT DOCUMENTS

| | | |
|---|---|---|
| CA | 2595233 | 7/2006 |
| CA | 2627555 | 5/2007 |
| DE | 195 46 692 A1 | 6/1997 |
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 100 34 105 C1 | 4/2002 |
| DE | 101 21 210 A1 | 11/2002 |
| DE | 19546692 C2 | 11/2002 |
| DE | 10301026 A1 | 2/2004 |
| DE | 10335948 B3 | 7/2004 |
| DE | 10302447 A1 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 202007005491 U1 | 7/2007 |
| EP | 0084395 A1 | 7/1983 |
| EP | 0458877 | 8/1990 |
| EP | 0402036 B1 | 12/1990 |
| EP | 0402176 B1 | 12/1990 |
| EP | 0 411 118 A1 | 2/1991 |
| EP | 0458877 B1 | 4/1991 |
| EP | 0515324 A1 | 11/1992 |
| EP | 0547135 B1 | 6/1993 |
| EP | 0 657 147 A2 | 6/1995 |
| EP | 0871414 | 9/1995 |
| EP | 0 592 410 B1 | 10/1995 |
| EP | 0756498 | 10/1995 |
| EP | 0 592 410 B1 | 11/1995 |
| EP | 0786970 | 5/1996 |
| EP | 0729364 B1 | 9/1996 |
| EP | 0756498 B1 | 5/1997 |
| EP | 0778775 B1 | 6/1997 |
| EP | 0786970 | 8/1997 |
| EP | 0888142 | 9/1997 |
| EP | 0971649 | 10/1998 |

(56) References Cited

FOREIGN PATENT DOCUMENTS

| | | |
|---|---|---|
| EP | 0928615 A1 | 7/1999 |
| EP | 1051204 | 7/1999 |
| EP | 1089676 | 12/1999 |
| EP | 0986348 B1 | 3/2000 |
| EP | 1117446 | 4/2000 |
| EP | 1 164 976 | 8/2000 |
| EP | 1158937 | 9/2000 |
| EP | 1 251 805 B1 | 10/2000 |
| EP | 1041942 B1 | 10/2000 |
| EP | 1041943 B1 | 10/2000 |
| EP | 1171061 | 10/2000 |
| EP | 1206179 | 2/2001 |
| EP | 1 233 731 | 5/2001 |
| EP | 1117446 B1 | 7/2001 |
| EP | 1 255 510 | 8/2001 |
| EP | 1259193 | 9/2001 |
| EP | 1 233 731 B1 | 5/2002 |
| EP | 1 330 213 | 5/2002 |
| EP | 1206179 B1 | 5/2002 |
| EP | 1347785 | 8/2002 |
| EP | 1235537 | 9/2002 |
| EP | 1248655 | 10/2002 |
| EP | 1251804 B1 | 10/2002 |
| EP | 1257305 | 11/2002 |
| EP | 0 971 649 B1 | 12/2002 |
| EP | 1395208 | 12/2002 |
| EP | 1 401 359 | 1/2003 |
| EP | 1406561 | 1/2003 |
| EP | 1281357 A2 | 2/2003 |
| EP | 1281375 A2 | 2/2003 |
| EP | 1408882 | 2/2003 |
| EP | 1 435 878 | 4/2003 |
| EP | 1 435 879 | 4/2003 |
| EP | 1 441 672 | 6/2003 |
| EP | 1 017 868 B1 | 9/2003 |
| EP | 1354569 A1 | 10/2003 |
| EP | 1494616 | 10/2003 |
| EP | 1 519 697 | 1/2004 |
| EP | 1 539 047 | 4/2004 |
| EP | 1551274 | 4/2004 |
| EP | 1 560 542 | 5/2004 |
| EP | 1414295 | 5/2004 |
| EP | 1 603 493 | 9/2004 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 663 070 | 3/2005 |
| EP | 1 253 875 B1 | 4/2005 |
| EP | 1 667 614 | 4/2005 |
| EP | 1 251 803 B1 | 6/2005 |
| EP | 1 702 247 | 7/2005 |
| EP | 1734902 | 8/2005 |
| EP | 1469797 B1 | 11/2005 |
| EP | 1835948 | 6/2006 |
| EP | 1863545 | 9/2006 |
| EP | 1893132 | 11/2006 |
| EP | 1901681 | 12/2006 |
| EP | 1 255 510 B1 | 3/2007 |
| EP | 1835948 | 9/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| FR | 2828263 A1 | 2/2003 |
| GB | 2433700 A | 7/2007 |
| GB | 2440809 A | 2/2008 |
| JP | 2003-523262 | 8/2003 |
| JP | 2003-524504 | 8/2003 |
| JP | 2005-118585 | 5/2005 |
| JP | 2007-296375 | 11/2007 |
| JP | 2008539305 | 11/2008 |
| WO | WO-90/09102 | 8/1990 |
| WO | WO 95/11055 A1 | 4/1995 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO-98/43556 | 10/1998 |
| WO | WO-98/46165 | 10/1998 |
| WO | WO-99/37337 | 7/1999 |
| WO | WO 99/53987 | 10/1999 |
| WO | WO 99/53987 A1 | 10/1999 |
| WO | WO-99/66863 | 12/1999 |
| WO | WO 00/02503 A1 | 1/2000 |
| WO | WO 00/15148 | 3/2000 |
| WO | WO-00/18445 | 4/2000 |
| WO | WO 00/25702 A1 | 5/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 01/35870 A1 | 5/2001 |
| WO | WO-01/41679 A1 | 6/2001 |
| WO | WO-01/51104 A1 | 7/2001 |
| WO | WO 01 54625 A1 | 8/2001 |
| WO | WO-01/58503 A1 | 8/2001 |
| WO | WO 01/62189 A1 | 8/2001 |
| WO | WO 01/64137 A1 | 9/2001 |
| WO | WO 02/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO-03/009785 A1 | 2/2003 |
| WO | WO 03/011195 A2 | 2/2003 |
| WO | WO 03/013239 | 2/2003 |
| WO | WO 03/028592 A1 | 4/2003 |
| WO | WO 03/047468 A1 | 6/2003 |
| WO | WO 03/051231 A2 | 6/2003 |
| WO | WO-03/079928 A2 | 10/2003 |
| WO | WO 03/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/062980 A2 | 7/2005 |
| WO | WO 2005/063980 A1 | 7/2005 |
| WO | WO-2005/072654 A1 | 8/2005 |
| WO | WO 2006/066327 | 6/2006 |
| WO | WO-2006/066327 A1 | 6/2006 |
| WO | WO 2006/076890 A1 | 7/2006 |
| WO | WO-2006/102063 A2 | 9/2006 |
| WO | WO 2006/108090 A2 | 10/2006 |
| WO | WO-2006/124649 A2 | 11/2006 |
| WO | WO 2006/124649 A2 | 11/2006 |
| WO | WO 2006/127756 A2 | 11/2006 |
| WO | WO 2006/127765 A2 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO-2008/028569 A1 | 3/2008 |
| WO | WO 2008/045949 | 4/2008 |
| WO | WO 2008/070797 A2 | 6/2008 |
| WO | WO 2006/076890 | 7/2008 |

(56) References Cited

FOREIGN PATENT DOCUMENTS

| WO | WO 2008/079962 A1 | 7/2008 |
|---|---|---|
| WO | WO 2008/101083 A2 | 8/2008 |
| WO | WO 2008/125153 A1 | 10/2008 |
| WO | WO 2008/138584 A1 | 11/2008 |

OTHER PUBLICATIONS

Ferrari, M. et al., "Transarterial Aortic Valve Replacement with a Self Expanding Stent in Pigs," Heart, vol. 90, pp. 1326-1331, (2004).

Aortenklappenbioprothese erfolgreich in der Entwicklung, (1 page) May 16, 2003.

Translation of Aortenklappenbioprothese erfolgreich in der Entwicklung (2 pages).

Screen shots from http://www.fraunhofer.de/presse/filme/2006/index.jsp (2 pages), 2006.

Liang, Ma, et al., "Double-crowned valved stents for off-pump mitral valve replacement," European Journal of Cardio-Thoracic Surgery, 194-198 (5 pages), Jun. 13, 2005.

Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.

Translation of DE 19546692 A1 (4 pages).

Translation of EP 1469797 B1 (16 pages).

\* cited by examiner (1:2)

CATHETER FOR THE TRANSVASCULAR IMPLANTATION OF PROSTHETIC HEART VALVES

The invention relates to catheters for the transvascular implantation of prosthetic heart valves with self-expanding anchoring systems, by means of which prosthetic heart valves can be implanted with minimal invasion.

It is becoming more frequently necessary for an increasing number of patients to have prosthetic heart valves implanted, for which purpose both artificial and biological implants are used for heart valve prostheses.

In the past, such operations have been conducted in such a way that it as necessary to use a heart-lung machine on the anaesthetised patient. This therefore makes it a cost-intensive surgical intervention, which subjects the respective patients to a high degree of psychological and physical stress. The aim is to keep the lethality risk below 3%. As the age of the respective patients increases and impairment of the respective heart valves becomes more advanced, a situation is reached in which patients in need of actual treatment become inoperable. Since surgical valve replacement is not possible for these patients, they suffer from a reduce quality of life and have a considerably reduced life expectancy. Intervention would pose an extremely high risk.

These same issues also apply to operations whereby prosthetic heart valves with anchoring systems are implanted by means of so-called balloon catheters.

In a procedure of this type, incorrect positioning can occur, which can have considerable consequences for the patient, possibly leading to the death of the respective patient.

In recent times, therefore, attempts have been made to implant heart valve prostheses by means of intervention methods involving minimal invasion, whereby such prostheses are fed together with an anchoring support via the aorta of a patient and through the aorta to the heart. On reaching the implantation site at the heart, self-expansion of such anchoring supports with a heart valve prosthesis attached to them is initiated, the intended result being a reliable anchoring and exact positioning of the heart valve prosthesis. Such anchoring supports have tended to be made from shape memory alloys, such as "Nitinol" for example, and the alloy is selected so that its transition temperature is around 37° C., and self-expansion can be initiated on reaching the transition temperature.

As a result of such expansion, the anchoring support opens up so that it is able to lie against the aorta wall, where it can be securely fixed by means of additional barb elements if necessary. The heart valve prosthesis is folded open simultaneously, so that it is able to assume its function.

An anchoring support of this type incorporating a heart valve prosthesis is described in patent specification WO 2004/019825 A1, for example.

Support hoops are provided at the proximal end of such an anchoring support, which can be introduced into the pockets of a patient's heart valve, thereby enabling the anchoring support to be very accurately positioned by means of these support hoops during a surgical intervention. What are referred to as commissural hoops are provided on this anchoring support in addition, which, together with the support hoops, clamp parts of a patient's old heart valve once the anchoring support has unfolded so that the anchoring support can be reliably positioned and secured as a result of this clamping effect.

The support and commissural hoops of this known anchoring support should therefore be disposed and dimensioned so that they permit a sequential self-expansion. This means that the anchoring support is accommodated inside a cartridge for the implantation procedure. It is then fed by means of a catheter through the aorta as far as the diseased heart. On reaching the implantation site, the cartridge is manipulated so that the support hoops are released to allow them to self-expand. The cartridge is then moved and oriented together with the anchoring support so that the support hoops are introduced into the pockets of the heart valve of the respective patient. This enables exact positioning to be achieved.

The respective cartridge is then further manipulated, so that the commissural hoops are also released and able to self-expand. As this happens, the old heart valve is clamped between the support and commissural hoops and the heart valve prosthesis is opened-up into its unfolded functional position.

After implanting the anchoring support incorporating the heart valve prosthesis, the catheter can then be removed from the patient's body together with the cartridge through the aorta.

Although the support hoops provided on the anchoring support can result in significantly easier and better positioning of the heart valve prosthesis to be implanted in the manner described above, there is a possibility of incorrect implantation and the heart valve prosthesis may not be capable of functioning or may be so to only an unsatisfactory degree. In certain situations, it is then no longer possible to remove a non-functioning or unsatisfactorily functioning heart valve prosthesis and it poses an increased risk of mortality for the respective patient in some cases.

The bend in the aorta in the human body during introduction through the aorta poses another problem during such surgical interventions. As the cartridge and the respective catheter are moved during this procedure, a change of direction of approximately 18° with a relatively small radius of about 50 mm has to be negotiated without causing damage to the vessel wall.

Accordingly, the objective of the invention is to reduce risk to the patient during implantation of prosthetic heart valves.

This objective is achieved by the invention on the basis of a catheter incorporating the characterising features defined in claim 1. Advantageous embodiments and designs of the invention may be obtained on the basis of the characterising features defined in the dependent claims.

In a preferred embodiment, a catheter proposed by the invention may be used in conjunction with a heart valve prosthesis with a self-expanding anchoring support of the type known from patent specification WO 2004/019825 and the disclosed contents are included herein by way of reference.

This being the case, the anchoring support with the heart valve prosthesis attached to it can be temporarily accommodated inside a cartridge unit in a collapsed state during the implantation.

A cartridge unit prepared in this manner can be releasably attached to the proximal end of a guide system. The cartridge unit and guide system are minimised in term of their external diameter to the degree that they can be fed through an aorta of a patient to be operated on without any difficulty, and to this end, the total free cross-section available inside the aorta should not be completely filled.

The guide system used is sufficiently long in terms of its length for the cartridge unit to be fed with the guide system by introducing it into the groin of a patient, through the aorta as far as the patient's heart.

A flexible, bendable region is provided on the guide system, by means of which a bending radius and bending angle can be achieved that will follow and make allowance for the bend in the patient's aorta.

Elements for operating the cartridge unit are fed by means of the guide system, which has a hollow interior. These operating elements enable parts of the cartridge unit to be manipulated and moved in a specific way. For example, a radial or also lateral movement of parts of the cartridge unit can be effected by means of the operating elements. Moving parts of the cartridge unit in this specific way enables parts of the anchoring support to be released in sequence so that implantation and anchoring can take place in the manner described in WO 2004/019825.

For example, support hoops of an anchoring support can be released by a rotation or by a lateral movement in the proximal or distal direction of a part of the cartridge unit, but other parts, such as the commissural hoops for example, continue to be retained inside the cartridge unit in the collapsed state, which can subsequently be released with a view to expansion by moving another part of the cartridge unit accordingly or by continuing the movement of the same part of the cartridge unit which previously still enabled the support hoops to be retained inside the cartridge unit in the collapsed state.

The heart valve prosthesis, which is attached to the anchoring support by stitching for example, opens simultaneously as the respective hoops of the anchoring support, to which the heart valve prosthesis is attached, expand.

In a preferred embodiment, in addition to the operating elements for parts of the cartridge unit, other operating elements are fed through the internally hollow guide system, which act on the bendable region in order to influence its curvature in a specific manner.

Due in particular to traction forces triggered via the operating elements, a specific curvature of the bendable region can be achieved during the implantation on penetrating the bend of the aorta. Tension cables or tension wires may be used as the operating elements, which are run through the internally hollow guide system as far as the proximal edge of the bendable region, where they are secured on the guide system, in which case the attacking points of the force of two such operating elements should be disposed diametrically opposite one another and in addition should be disposed at 90° with respect to the bending axis about which the bendable region is required to curve.

For example, the curvature of the bendable region can be influenced in a specific way by applying a traction force via one of the operating elements as the guide system is pushed through the bend in the aorta by means of the bendable region and pulled out of it once the implantation has been completed.

The bendable region of a guide system may be provided in the form of a link chain, in which the individual links are connected to one another by individual joints. This being the case, the individual joints positively engage in respective adjacent links. They are designed so that a curvature of more than 180° can be maintained in the bending region, with a bending radius which guarantees that at least the radius of the bend in the aorta can be achieved.

The individual joints on the individual links of a link chain should also be disposed diametrically opposite one another in pairs on the individual links and parallel with the rotation axis of the bendable region.

The guide system used with a catheter proposed by the invention should advantageously also be designed so that a liquid coolant or a pharmaceutical preparation can be circulated through the internally hollow guide system as far as the cartridge unit. With the aid of such a liquid coolant, for example a salt solution, the anchoring support can be kept below the transition temperature of the shape memory alloy. This also prevents body fluids from being able to penetrate the interior of the guide system and a liquid pressure should therefore be maintained which lends a sufficiently high resistance to penetration by body fluid or other elements contained in body fluid.

Introducing liquid coolant in an appropriate manner can also prevent gas, for example air, from getting into the aorta and the blood.

To this end, the entire guide system should be as liquid-proof as possible. Accordingly, a flexible, bendable region provided in the form of a link chain in this instance may be sealed from the outside by means of a plastic hose to render it liquid-proof.

The parts of the cartridge unit which can be moved in a specific way in order to release hoops of the anchoring support are preferably provided in the form of sleeve-shaped elements, the internal and external diameters of which are adapted to one another so that they can engage in one another telescopically, and at least two of the sleeve-shaped elements have mutually adapted internal and external diameters such that a collapsed anchoring support with heart valve prosthesis can be accommodated between them and retained in the collapsed state.

When introducing the catheter, the cartridge unit should be completely closed as far as possible and to facilitate introduction through the aorta should have a tip at its proximal end, which is in turn preferably made from a flexible material, for example silicone.

When the cartridge unit reaches the respective patient's heart, the appropriate manipulation can then be performed, in other words parts/sleeve-shaped elements of the cartridge unit moved, so that the different hoops of the anchoring support are sequentially released and the heart valve prosthesis secured to them simultaneously opened up.

As this happens, however, the anchoring support is still securely retained on the cartridge unit. To this end, anchoring elements are provided on one sleeve-shaped element of the cartridge unit, disposed at the distal end, for example at a point where eyes are provided on the anchoring support. In this position, these anchoring elements together with the distal part of the anchoring support are also covered by a sleeve-shaped element of the cartridge unit, so that the distal part of the anchoring element is still retained in the collapsed state.

In this position, it is possible to check the function of the heart valve prosthesis, which has already unfolded. Once it is evident that the heart valve prosthesis is functioning, a further manipulation may be effected by moving the sleeve element that was previously covering the anchoring element with the distal part of the anchoring support accordingly, which causes the distal part of the anchoring support to be fully released as well so that it can then fully unfold.

If, on checking, it is found that the implanted heart valve prosthesis is not fulfilling its function or is so but not satisfactorily, it is advantageously possible to move the anchoring support together with the heart valve prosthesis back into the cartridge unit by moving the parts/sleeve-shaped elements in the opposite direction accordingly and removing all the parts, in other words the entire catheter, from the patient's body again, thereby significantly reducing the risk of the operation, after which a further attempt at implantation can be made on the same patient.

In one advantageous embodiment of the catheter proposed by the invention, a guide wire can also be run through the entire catheter. Such guide wires are already used for operations of this type and they are fed through the patient's aorta to a point behind the heart before introducing the catheter. The catheter can then be placed over the cartridge unit and guide system and into the guide wire and pushed in along it into the aorta as far as the patient's heart.

In order to monitor the process of introducing the catheter and also manipulation of the bendable region, in particular at the bend of the aorta, it is of advantage to provide marker elements on the guide system and/or the cartridge unit, made from a material which absorbs X-radiation, so that the respective position can be pinpointed on an X-ray image during the operation.

A screen filter may also be used with the catheter proposed by the invention, by means of which particles can be prevented from penetrating the respective patient's blood circulation system. Such a screen filter may be attached to the guide system so that it completely surrounds it in the radial direction. In this respect, it should be elastically biased so that it lies against the vessel wall of the aorta, thereby guaranteeing a closure that is impermeable to particles.

Furthermore, the catheter proposed by the invention may additionally be provided with a conventional balloon disposed in the interior of the guide system or cartridge unit and carried with it there or alternatively it can be fed through the interior of the guide system as far as the anchoring support to be expanded. Using such a balloon, the volume of which can be increased by means of a fluid at increased pressure, will further assist expansion of the anchoring support.

The operating elements described above, which may be fed through the interior of the guide system and provided in the form of traction and compression means, may advantageously be manipulated from a manipulating part. The manipulating part may be designed as a handle, by means of which the movement for introducing the catheter can then be effected by the respective surgeon.

Other control elements are also provided on such a manipulating part, by means of which the respective movement of the operating elements can be initiated. This being the case, it should be possible to effect the corresponding movement in as measured a manner as possible, for example with appropriate translation ratios, and it should be possible to restrict the respective movement by end stops or catch positions at least. This enables specific maximum distances or angles to be preserved, for which allowance can be made in achieving the sequential expansion of the anchoring support or the specific way in which the curvature of the bendable region is influenced. In this respect, it should be possible to adjust the end stops or individual catches as finely as possible.

All the parts of a catheter proposed by the invention but at least those which come into direct contact with the respective patient and are also introduced into the aorta should be made from bio-compatible materials which are compatible with the respective organism. It should also be possible to sterilise them, in which case it should be possible to use one of the standard sterilisation processes.

The invention will be explained in more detail on the basis of examples.

Of the drawings:

FIGS. 1 to 4 are intended to illustrate and provide a clearer understanding of an example of a catheter proposed by the invention. The individual diagrams illustrate different phases which take place during implantation of an anchoring support 10 incorporating a heart valve prosthesis.

Figure 1:
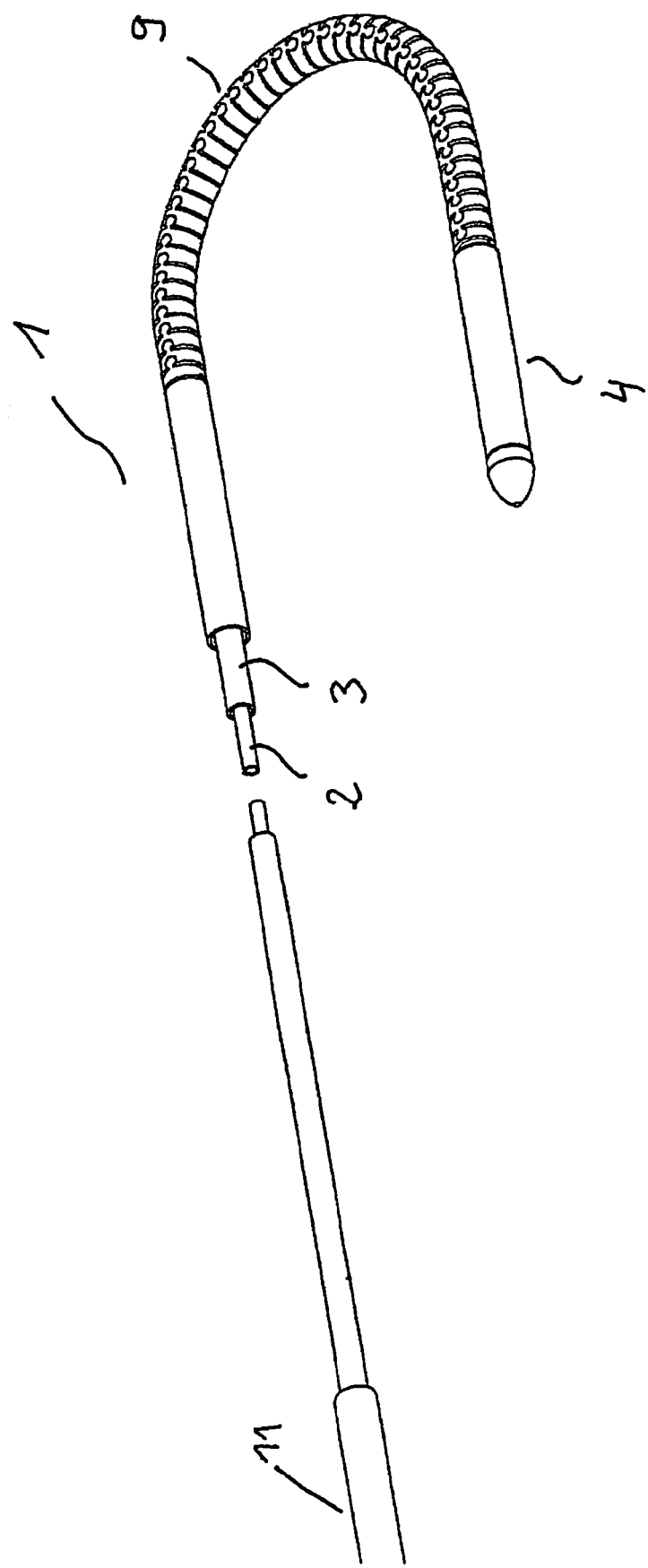
FIGS. 1 to 4 are schematic diagrams illustrating an example of a catheter proposed by the invention during different possible phases of an implantation procedure.

The example of a catheter proposed by the invention illustrated in FIG. 1 is shown with the cartridge unit 4, which is still completely closed, containing an anchoring support 10 incorporating a heart valve prosthesis in the non-expanded state and thus collapsed, so that it can be fed by means of the internally hollow guide system 1 through an appropriate access into the aorta and through it to the respective implantation site on the patient's heart.

Proximally disposed on the cartridge unit 4 is a flexible tip made from silicone, which facilitates the introduction procedure and reduces the risk of damage.

Part 5 of the cartridge unit is releasably connected to the other parts of the guide system 1, for example by means of a screw connection.

Adjoining the cartridge unit 4 is a bendable region 9, which is designed and dimensioned so that it is guaranteed to be able to move through the bend of a patient's aorta without causing problems.

Possible designs of such a bendable region 9 will be explained below.

Other parts of the internally hollow guide system 1 are also illustrated and FIGS. 1 to 4 show two operating elements 2 and 3 running through the guide system 1 as far as the cartridge unit 4, and in this instance the operating element 2 likewise runs through the internally hollow operating element 3 as far as the cartridge unit 4.

The operating elements 2 and 3 in this instance are provided in the form of lengths of compression spring, which are preferably reinforced by means of tension wire. Such tension wires make the catheter safer as it is being removed from the patient's body once the operation is complete.

Other parts 11 of the guide system 1 are illustrated on the left-hand side, which may be provided in the form of more or fewer sleeve-shaped parts, although these must be secured so that they are sufficiently pressure- and tension-resistant to withstand introduction into the aorta and extraction from the aorta again. Appropriately stiff plastic hoses may be used for this purpose, for example PTFE hoses or hoses with a PTFE base, because they are sufficiently compatible with the organism and can also be sterilised.

Figure 2:
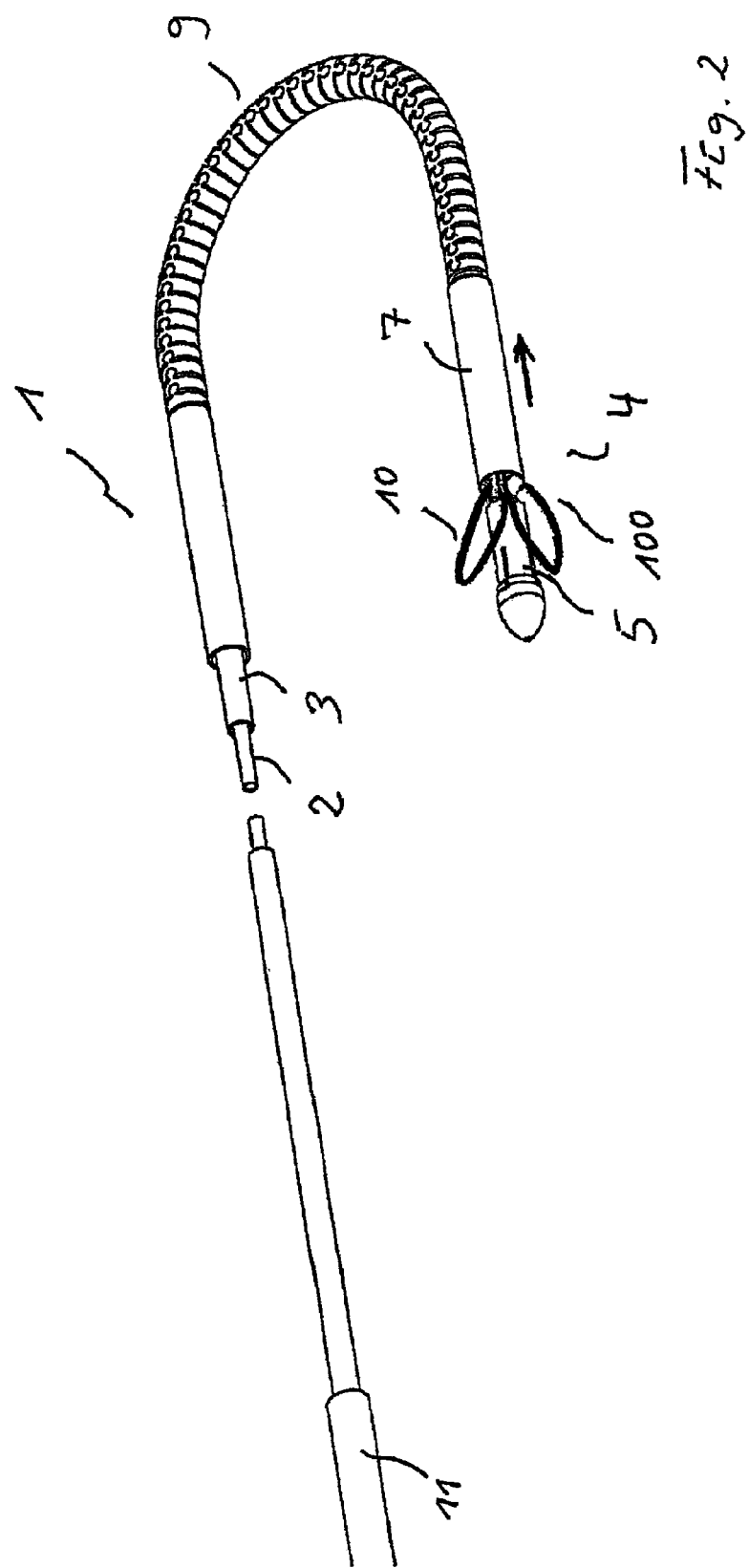

FIG. 2 illustrates the procedure which takes place during a first stage of the operation on reaching the implantation site on the respective patient's heart. The part/sleeve-shaped element 7 of the cartridge unit 4 can be pulled back in the distal direction by a distal movement of one of the operating elements 2 and/or 3 so that some hoops 100 of the anchoring support 10, for example and preferably the support hoops provided on the known heart valve prosthesis disclosed in WO 2004/019825 A1, expand and are biased radially outwards.

The entire catheter with the guide system 1 and the cartridge unit 4 can therefore be pushed proximally and these hoops (support hoops) introduced into the pockets of the patient's old heart valve. When the surgeon feels a perceptible resistance, the process of introducing the support hoops of the anchoring support 10 into the pockets of the old heart valve is complete.

The part/sleeve-shaped element 5 of the cartridge unit 4 can then be moved proximally forwards, so that other hoops of the anchoring support can then also be released so that they can self-expand and open up the heart valve prosthesis.

Figure 3:
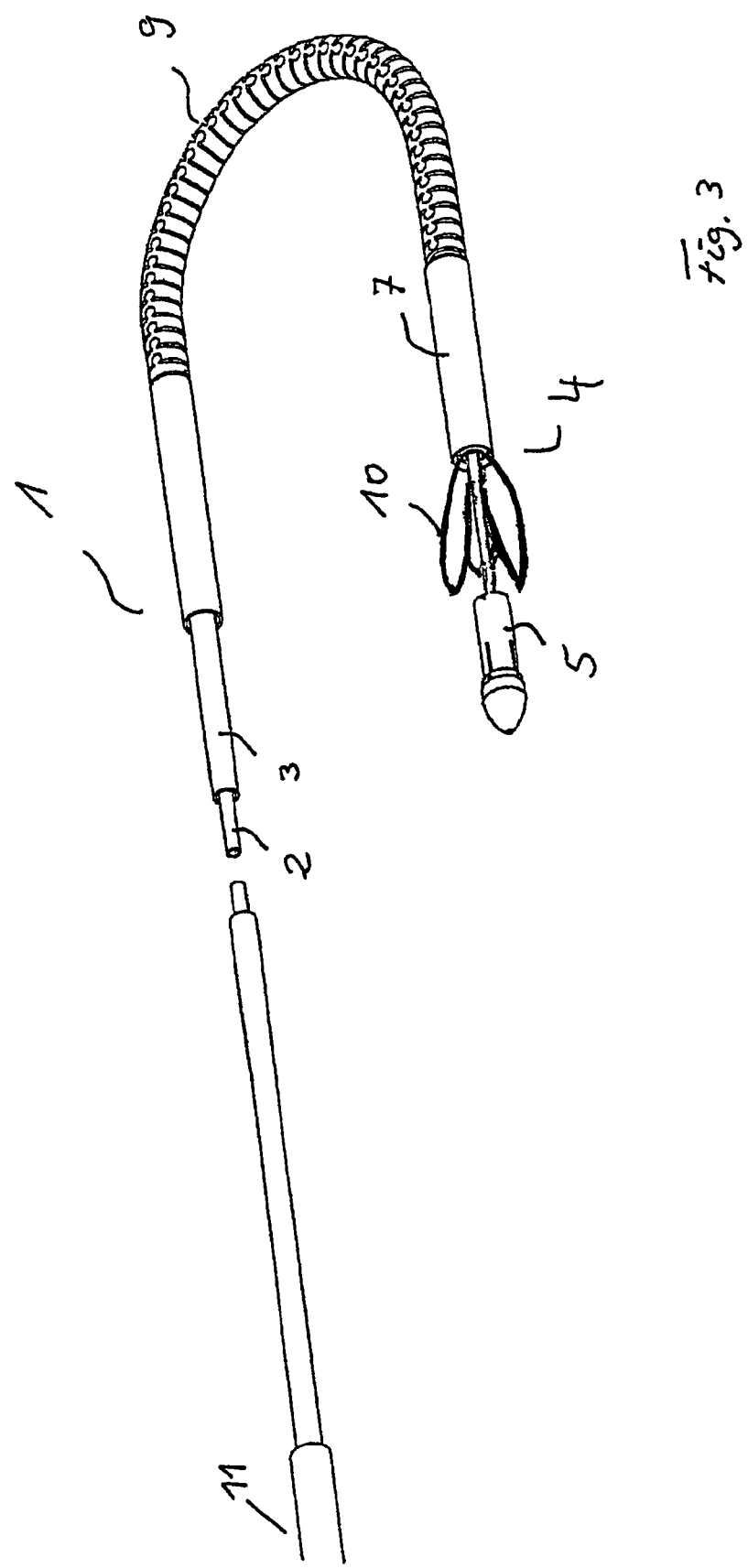

A preliminary stage of this is illustrated in FIG. 3, where a heart valve prosthesis has not yet been fully unfolded and the anchoring support 10 can also not yet be fully anchored.

As also illustrated in FIG. 3, a distal part of the anchoring support 10 is still accommodated inside the cartridge unit 4, underneath the part/sleeve-shaped element 7 in the cartridge unit 4. This remains the case until the process of unfolding and positioning the heart valve prosthesis has reached the stage where its functionality can be checked.

If the check reveals incorrect functioning or faulty positioning, the part/sleeve-shaped element 7 can be pushed proximally again by one of the two operating elements 2 or 3 so that the anchoring support 10 with the heart valve prosthesis is at east partially accommodated in the cartridge unit 4 again and then the entire catheter can be removed from the patient by pulling it out of the aorta without causing damage to the vessel wall.

Figure 4:
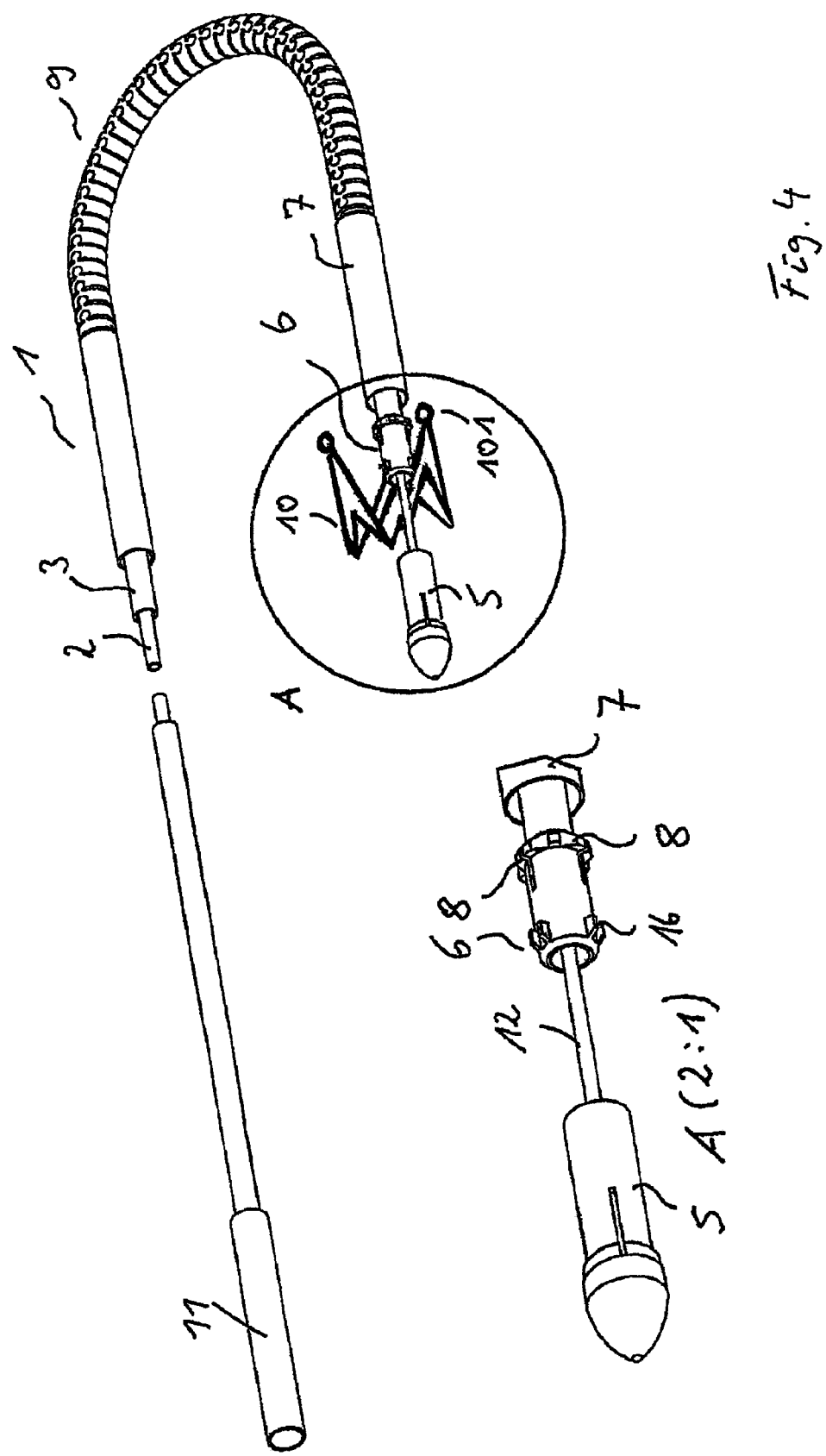

If the function test reveals that the heart valve prosthesis is able to fulfil its function to at least a sufficient capacity, the part/sleeve-shaped element 7 may be moved distally back, as illustrated in FIG. 4, or another part/sleeve-shaped element 6 of the cartridge unit 4 may be pushed in the proximal direction so that the distal part of the anchoring support 10 can also be released and expand fully.

As also illustrated in FIG. 4, eyes 101 or other appropriate elements are provided at distal end regions of the anchoring support 10, which were previously engaged in anchoring elements 8 provided on the part/sleeve-shaped element 6. These eyes and the anchoring elements 8 ensure reliable retraction or extraction if it is established that an anchoring support 10 incorporating a heart valve prosthesis has been incorrectly or badly implanted, enabling the anchoring support 10 and heart valve prosthesis to be removed from the patient's body.

By means of the anchoring elements 8 as well as other guide elements 16 which may optionally be provided on the part/sleeve-shaped element 6 of the cartridge unit 4, it is also possible to effect a radial turning movement to enable the hoops of an anchoring support 10 to be introduced into the pockets of an old heart valve prosthesis in an exactly correct angular position, for example, in which case the entire catheter can be turned slightly about its longitudinal axis by the surgeon during the implantation.

Detail A of FIG. 4 also specifically illustrates a cannula 12, which is fed through the cartridge unit 4 along its longitudinal axis. By mans of the cannula 4, the guide wire described in the general part of the description can be fed through cartridge unit 4.

Figure 5:
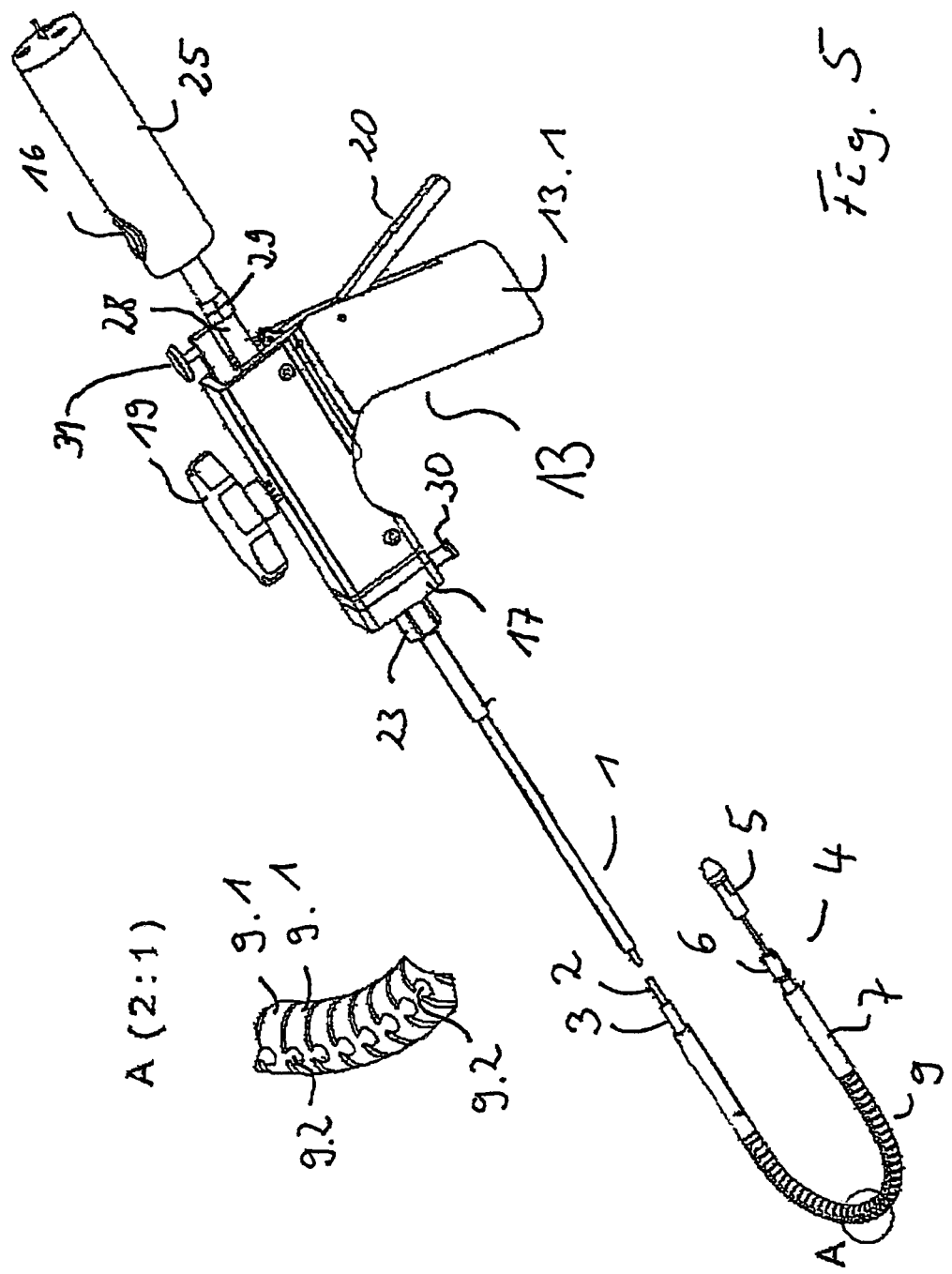
FIG. 5 shows an example of a catheter with a manipulating part.

FIG. 5 illustrates an example of a catheter with an additional manipulating part 13, on which other control elements are provided in order to permit manipulation.

The guide system 1 together with the cartridge unit 4 described above with reference to FIGS. 1 to 4 are also used in this example.

However, detail A illustrates one possible design of the bendable region 9 in the form of a link chain.

The individual links 9.1 are generally of the same shape and dimension.

In this respect, the oppositely lying end faces of the individual links 9.1 are shaped so as to form individual joints 9.2, each of which positively engages in adjacent individual links 9.1 and as a result of gaps with a sufficient gap width between the individual links 9.1 respectively ensure that the bendable region bends about at least 1800 as mentioned above, with a radius of approximately 50 mm.

The individual joints 9.2 are formed by a cut-out in the respective oppositely lying end faces of the individual links 9.1, whereby a co-operating cut-out on one end face and a co-operating rounded, complementary protruding area on the diametrically opposite end face of the individual links 9.1 form the individual joints 9.2 on respective adjacent individual links 9.1.

Although not illustrated, the bendable region 9 may be enclosed by a plastic hose to render it fluid-tight.

FIG. 5 also illustrates how a manipulating part 13 may be provided to enable a catheter proposed by the invention to be introduced and manipulated.

A handle 13.1 is provided for introducing and extracting the catheter with the guide system 1 and cartridge unit 4.

A fluid-tight closure in the form of a plate 17 is provided in the proximal part of the manipulating part 13, enabling the guide system 1 to be flange-mounted by means of a locking nut 23, and seal elements are provided, although these are not illustrated here.

A standard Luer connection 30 is also provided, by means of which the coolant liquid can be circulated.

Figure 6:
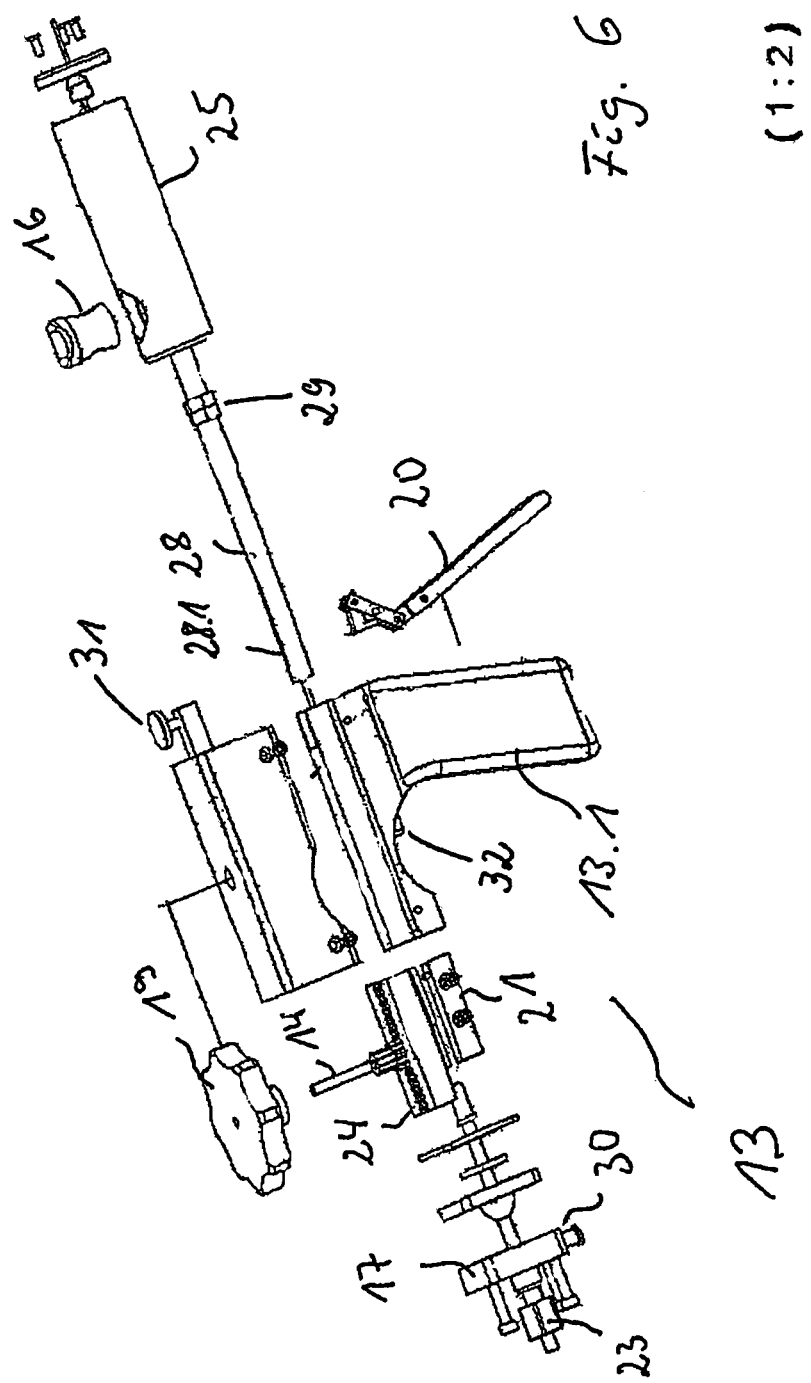
FIG. 6 is an exploded diagram illustrating the manipulating part illustrated in FIG. 5.

The respective curvature of the bendable region 9 can be obtained using the handle 19, which can be turned about an axis by means of tension cables (not illustrated) and this will be further explained with the description of FIG. 6.

The entire manipulating part 13 should be sealed with respect to the surrounding environment and with respect to the guide system 1 so that it is as far as possible fluid-tight and also gas-tight if necessary.

The tube 28 can be moved laterally in the proximal direction by means of the lever 20 acting on the handle 13.1, and the corresponding movement and resultant traction or compression force transmitted to one of the two operating elements 2 and/or 3, thereby enabling a manipulation of the individual parts/sleeve-shaped elements 5, 6 and/or 7 of the cartridge unit 4 in the manner described above, for example in finely measured doses via the pumping movements of the lever 20.

The pushing handle 25 enables the position of part 5 of the cartridge unit 4 to be manipulated relative to the sleeve-shaped part 6 of the cartridge unit 4 in the extension beyond the length of spring by means of the fixing hooks, serving as anchoring elements 8. The pushing handle 25 is latched in a thread-shaped toothing 28.1 of a tube 28 by means of a compression spring. As a result, the pushing handle 25 follows the proximal movement of the tube 28, which is connected to part 6 of the cartridge via the length of spring serving as an operating element 3.

On reaching an end stop marking the first discharge stage, the pushing handle 25 can be turned in order to effect a finely measured axial displacement of part 5 of the cartridge unit 4 relative to part 6 of the cartridge unit 4 in the direction of the pitch of the thread 28.1.

With respect to operating the pushing handle 25, the latter is able to move the part 5 of the cartridge unit 4 illustrated here without an additional fine adjustment.

Such a manipulation enables the anchoring support 10 to be released (see FIG. 3) and in this position, the anchoring support 10 can still be retracted.

When the stop 29 is released by means of an actuator member 31 provided in the form of an adjusting screw for example, the cartridge unit 4 may be extracted farther by operating the lever system 20 in the manner described above until the retaining eyes of the anchoring support 10 have moved away from the cartridge unit 4 and the anchoring support 10 is able to spring away from the anchoring elements 8 due to its expansion forces.

The elements of the cartridge unit 4 may be pulled back in stages. This being the case, part 5 of the cartridge unit 4 may be retracted by pulling back the pushing handle 25 (pushing element latched) beyond part 6 of the cartridge unit 4.

By operating a releasing bolt 32, part 6 of the cartridge unit 4 connected to the tube 28 can also be returned to its initial position by pulling the pushing handle 25 farther back so that the cartridge unit 4 is then completely closed again. In this state, the catheter can be removed from the patient's body again.

FIG. 6 is an exploded diagram providing a more detailed illustration of the manipulating part 13 used in this example.

As illustrated, when the handwheel 19 is turned via the shaft 14, two toothed racks 24 oriented parallel with one another can be displaced. Accordingly, one toothed rack 24 is moved in the proximal direction as the toothed rack 24 oriented parallel with it is moved in the distal direction.

Although these are not illustrated here, tension cables may be secured to clamping jaws 21 acting on the co-operating toothed racks 24, which are fed through the internally hollow guide system 1 as far as the bendable region 9 and are preferably secured in its proximal region.

By turning the handwheel 19 accordingly, a traction force can be applied to at least one of the two tension cables, causing the bendable region 9 to assume the appropriate curvature in measured doses so that the guide system 1 can be fed through the bend of the aorta in a defined manner together with the cartridge unit 4.

As also illustrated in FIG. 6, the lever 20 connected to the handle 13.1 acts via fine toothing 28.1 on the tube 28, enabling it to be manipulated via the operating elements 2 and/or 3 to permit the sequential release of the anchoring support 10.

The invention claimed is:

1. Catheter for the transvascular implantation of a valve prosthesis having a prosthetic valve attached to a support element, comprising:
    a cartridge unit holding the valve prosthesis in a collapsed state, the valve prosthesis comprising a first plurality of support hoops with attachment elements on end regions of the support hoops, the cartridge unit comprising a first sleeve-shaped element including anchoring elements on a distal region, wherein the attachment elements engage the anchoring elements, a second sleeve-shaped element, and a third sleeve-shaped element configured to at least partially surround the valve prosthesis such that the support hoops are radially inward of the third sleeve-shaped element; and
    operating elements disposed within a hollow guide system and extending to the cartridge unit, wherein the operating elements are configured to affect movement of the cartridge unit rotatably about its longitudinal axis to affect movement of the valve prosthesis rotatably and axially along its longitudinal axis;
    wherein axial movement between the second and third sleeve-shaped elements in substantially opposite directions is configured to affect a sequential release of the valve prosthesis from a collapsed state to an expanded state.

2. Catheter as claimed in claim 1, further including a bendable region.

3. Catheter as claimed in claim 2, wherein the bendable region includes a plurality of joints and is configured to affect a bend in the catheter of 180 degrees.

4. Catheter as claimed in claim 1, wherein the catheter is configured such that a liquid coolant is circulated through an interior of the hollow guide system as far as the cartridge unit.

5. Catheter as claimed in claim 4, wherein the hollow guide system is configured to be liquid-proof.

6. Catheter as claimed in claim 1, wherein the second and third sleeve-shaped elements are telescopically disposed with respect to one another, and wherein the valve prosthesis is held in the collapsed state by the first and second sleeve-shaped elements.

7. Catheter as claimed in claim 6, wherein the third sleeve-shaped element is movable in a distal direction to permit the first plurality of support hoops to self-expand while the second sleeve-shaped element maintains the remainder of the valve prosthesis in the collapsed state.

8. Catheter as claimed in claim 7, wherein the second sleeve-shaped element is movable in a proximal direction to permit the remainder of the valve prosthesis to self-expand.

9. Catheter as claimed in claim 1, wherein the plurality of anchoring elements are configured to permit rotation of the support element about a longitudinal axis of the catheter.

10. Catheter as claimed in claim 1, wherein the first plurality of support hoops are configured to be positioned within a plurality of pockets of a native valve.

11. Catheter as claimed in claim 1, wherein the valve prosthesis further includes a body portion, and the first plurality of support hoops and the body portion are configured to clamp at least a portion of native valve leaflets when the valve prosthesis is implanted.

12. A catheter for implanting a valve prosthesis, comprising:
    a cartridge unit configured to hold the valve prosthesis in a collapsed state, the valve prosthesis comprising a plurality of support hoops with attachment elements on end regions of the support hoops, the cartridge unit comprising:
    a first sleeved-shaped element comprising anchoring elements on a distal region, wherein the attachment elements engage the anchoring elements;
    a second sleeve-shaped element; and
    a third sleeve-shaped element configured to at least partially surround the valve prosthesis such that the plurality of support hoops are radially inward of the third sleeve-shaped element;
    wherein relative axial movement between the second and third sleeve-shaped elements in substantially opposite directions is configured to permit sequential expansion of the valve prosthesis from a collapsed form to an expanded form.

13. The catheter of claim 12, wherein axial movement of the third sleeve-shaped element in a distal direction relative to the first sleeve-shaped element permits the plurality of support hoops to radially expand from the collapsed form to the expanded form.

14. The catheter of claim 13, wherein axial movement of the second sleeve-shaped element in a proximal direction relative to the first sleeve-shaped element permits a body portion of the valve prosthesis to radially expand from the collapsed form to a partially expanded form.

15. The catheter of claim 14, wherein axial movement of the third sleeve-shaped element in the proximal direction relative to the first sleeve-shaped element collapses the plurality of support hoops.

16. The catheter of claim 14, wherein further axial movement of the third sleeve-shaped element in the distal direction relative to the first sleeve-shaped element permits the plurality of attachment elements to expand.

17. The catheter of claim 14, wherein relative axial movement of the first sleeve-shaped element in the proximal direction relative to the third sleeve-shaped element permits the plurality of attachment elements to expand.

18. The catheter of claim 12, wherein the first sleeve-shaped element and the valve prosthesis are configured to rotate about a longitudinal axis.

19. Catheter as claimed in claim 12, wherein the plurality of support hoops are configured to be positioned within a plurality of pockets of a native valve.

20. The catheter of claim 12, wherein the valve prosthesis further includes a body portion, and the plurality of support hoops and the body portion are configured to clamp at least a portion of native valve leaflets when the valve prosthesis is implanted.

21. A catheter for implanting a valve prosthesis including a support element and a prosthetic valve attached to the support element, comprising:
 a cartridge unit disposed between proximal and distal ends of the catheter configured to selectively retain the valve prosthesis in a collapsed form, the valve prosthesis comprising:
 a distal end, a proximal end, and a plurality of support hoops extending from the distal end of the support element toward the proximal end of the support element, the support hoops having attachment elements on end regions of the support hoops;
 the cartridge unit comprising:
 a first sleeve-shaped element comprising anchoring elements on a distal region, wherein the attachment elements engage the anchoring elements, a second sleeve-shaped element, and a third sleeve-shaped element configured to at least partially surround the valve prosthesis such that the plurality of support hoops are radially inward of the third sleeve-shaped element, wherein axial movement of the second and third sleeve-shaped elements in substantially opposite directions is configured to permit sequential expansion of the valve prosthesis from a collapsed state to an expanded state such that the plurality of support hoops are biased radially outward and configured to be positioned on a first side of a leaflet of a native valve and a remainder of the valve prosthesis is biased radially outward and configured to be positioned on a second side of the leaflet of the native valve, opposite the first side.

22. The catheter of claim 21, wherein the first sleeve-shaped element is configured to affect rotation of the valve prosthesis about a longitudinal axis of the cartridge unit.

23. The catheter of claim 21, wherein the cartridge unit is further configured to affect expansion of the remainder of the valve prosthesis after expansion of the plurality of support hoops.

24. The catheter of claim 21, wherein the expanded plurality of support hoops and the fully expanded remainder of the valve prosthesis are configured to clamp at least a portion of the native heart valve.

25. A catheter for implanting a valve prosthesis including a prosthetic valve attached to a support structure having a body portion and a plurality of support hoops with attachment elements on end regions of the support hoops, the catheter comprising:
 a first sleeve-shaped element comprising anchoring elements on a distal region, wherein the attachment elements engage the anchoring elements;
 a second sleeve-shaped element; and
 a third sleeve-shaped element configured to at least partially surround the valve prosthesis such that the support hoops are radially inward of the third sleeve-shaped element;
 wherein the is plurality of support hoops are connected to the body portion at a distal end of the body portion and extend toward a proximal end of the body portion; and
 wherein axial movement of the second and third sleeve-shaped elements in substantially opposite directions is configured to permit sequential expansion of the valve prosthesis from a collapsed state to an expanded state.

26. The catheter of claim 25, wherein the expanded support hoops are configured to be positioned in pockets of a native heart valve.

27. The catheter of claim 25, wherein the expanded plurality of support hoops and the expanded body portion are configured to clamp a native valve.

28. A catheter for transvascular implantation of a valve prosthesis including a self-expanding anchoring support having a body portion and a plurality of support hoops and a prosthetic valve attached to the anchoring support with attachment elements on end regions of the support hoops, the catheter comprising:
 (a) a cartridge unit for carrying the anchoring support and prosthesis and having a flexible tip at its proximal end, the cartridge unit comprising a first sleeve-shaped element including anchoring elements on a distal region, wherein the attachment elements engage the anchoring elements, a second sleeve-shaped element, and a third sleeve-shaped element configured to at least partially surround the valve prosthesis such that the support hoops are radially inward of the third sleeve-shaped element, wherein axial movement of the second and third sleeve-shaped elements in substantially opposite directions is configured to permit sequential expansion of the valve prosthesis from a collapsed state to an expanded state;
 (b) a hollow guide system releasably connected to the cartridge unit at a proximal end of the hollow guide system; and
 (c) a manipulating part attached to a distal end of the hollow guide system wherein operating elements are attached at one end to the manipulating part and at the other end to the cartridge unit, the hollow guide system has a bendable region at its proximal end adjacent to the cartridge unit, the hollow guide system is configured to contain a circulating coolant or pharmaceutical preparation; and the guide system is substantially liquid proof.

29. Catheter as claimed in claim 28, wherein the bendable region includes a link chain with individual joints.

30. Catheter as claimed in claim 29, wherein the individual joints positively engage respectively in adjacent links.

31. Catheter as claimed in claim 28, wherein the operating elements include tension wires.

32. Catheter as claimed in claim 28, wherein the guide system is configured to circulate the liquid coolant through an interior of the guide system to the cartridge unit.

33. Catheter as claimed in claim 28, wherein the second and third sleeve-shaped elements are telescopically engaging in one another, between which the valve prosthesis is enclosed and clamped in the collapsed state until implantation.

34. Catheter as claimed in claim 28, wherein the catheter is configured for guiding a guide wire through an interior of the catheter.

\* \* \* \* \*

UNITED STATES PATENT AND TRADEMARK OFFICE
CERTIFICATE OF CORRECTION

| | | |
|---|---|---|
| PATENT NO. | : 8,679,174 B2 | Page 1 of 1 |
| APPLICATION NO. | : 11/795590 | |
| DATED | : March 25, 2014 | |
| INVENTOR(S) | : Ottma et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1818 days.

Signed and Sealed this
Twenty-first Day of July, 2015

Michelle K. Lee
*Director of the United States Patent and Trademark Office*